United States Patent [19]
Gazit et al.

[11] Patent Number: 5,496,523
[45] Date of Patent: Mar. 5, 1996

[54] FILTERED MICROPIPETTE TIP FOR HIGH/LOW VOLUME PIPETTORS

[75] Inventors: Arnona Gazit, Holon; Abraham Yaniv, Tel-Aviv, both of Israel

[73] Assignee: Sorenson Bioscience, Salt Lake City, Utah

[21] Appl. No.: 239,477

[22] Filed: May 6, 1994

[51] Int. Cl.⁶ ............................... B01L 3/02; B01L 11/00
[52] U.S. Cl. .................. 422/100; 422/101; 73/864.01; 73/864.02; 73/864.03; 73/864.11
[58] Field of Search ................... 422/100, 101; 73/864.01, 864.02, 864.03, 864.11

[56] References Cited

U.S. PATENT DOCUMENTS

| | | | |
|---|---|---|---|
| 4,466,298 | 8/1984 | Tervamaki et al. | 73/864.18 |
| 4,483,825 | 11/1984 | Fatches | 422/100 |
| 4,707,337 | 11/1987 | Jeffs et al. | 422/100 |
| 4,863,695 | 9/1989 | Fullemann | 422/100 |
| 4,999,164 | 3/1991 | Puchinger et al. | 422/100 |
| 5,156,811 | 10/1992 | White | 422/100 |
| 5,171,537 | 12/1992 | Wainwright et al. | 422/100 |
| 5,192,511 | 3/1993 | Roach | 422/100 |
| 5,200,151 | 4/1993 | Long | 422/100 |
| 5,223,225 | 6/1993 | Gaitsch | 422/100 |
| 5,232,669 | 8/1993 | Pardinas | 422/100 |
| 5,240,679 | 8/1993 | Stettler | 422/67 |
| 5,260,030 | 11/1993 | De Vaughn | 422/100 |
| 5,272,926 | 12/1993 | Wilkins | 73/864.13 |
| 5,334,353 | 8/1994 | Blattner | 422/100 |

FOREIGN PATENT DOCUMENTS

| | | |
|---|---|---|
| 0148333 | 7/1985 | European Pat. Off. |
| 2164585 | 3/1986 | United Kingdom. |
| 2211111 | 6/1989 | United Kingdom. |
| 9116975 | 11/1991 | WIPO. |

Primary Examiner—Timothy M. McMahon
Assistant Examiner—N. Bhat
Attorney, Agent, or Firm—Thorpe, North & Western

[57] ABSTRACT

A micro volume, filtered pipette tip device useful with either of two respective pipettors comprising (i) a manual or electronic, air displacement pipettor operable within the approximate range of 0 to 20 microliters and having a relatively long insert tip, and (ii) a manual or electronic, air displacement pipettor operable within the approximate range of 20 to 200 microliters and having a relatively short insert tip. The filtered pipette tip device includes a pipette tip body having insert and fill chambers extending in continuous tapering configuration from the mounting end to the fluid contacting end. A filter is positioned within the axial bore in the intermediate section, providing a dividing barrier between the insert and fill chambers of the pipette tip device. The insert chamber includes a tapering internal wall structure configured to receive a continuously tapering terminal insert portion of each of the two respective pipettors in a snug, sealed fit within the insert chamber. The filter is positioned sufficiently deep within the axial bore and intermediate section of the pipette tip device to allow the terminal end of the insert portion of either of the two respective pipettors to seat within the insert chamber without contacting the filter means.

16 Claims, 2 Drawing Sheets

FILTERED MICROPIPETTE TIP FOR HIGH/LOW VOLUME PIPETTORS

FIELD OF THE INVENTION

This invention relates to pipette tips used with manual, air displacement, micropipetting devices within the range of zero to 200 microliters. More particularly, the present invention pertains to a single pipette tip which effectively services both a standard 20 microliter pipettor, 100 microliter pipettor and a 200 microliter pipettor without need for an adaptor or other modifying structure.

Prior Art

Small quantities of liquid specimens which require controlled handling and transfer as part of chemical, biological or medical diagnosis or testing procedures are often processed by pipetting an aliquot portion of the specimen to a reaction vial. The need for accuracy in drawing and dispensing such specimens has led to use of different sized pipettors specifically suited to a given range of fluid. For example, micropipetting is generally considered to extend within the range from zero to 200 microliters. In contrast macropipetting spans the range of 1.0 ml to 5 ml.

Within the micropipetting range, a further standard classification has developed comprising a "low" volume range extending from 0 to 20 microliters and a "high" volume range of 20 to 200 microliters. These high and low volume pipetting classifications are currently serviced by two different pipettors represented by instruments sold under the trademark GILSON PIPETMAN, respectively identified as models P200 and P20. A P100 instrument is also available for 0–100 microliters and is of comparable design. These P200 and P20 devices 10 and 11 are illustrated in FIGS. 1 and 2, and account for over 75% of the pipettors currently in use within the manual micropipetting industry. The remaining competing instruments have a similar configuration and are similarly designed to operate within the respective high and low volume ranges. Indeed, this protocol has become the worldwide standard used by every lab. Virtually every technique, apparatus, reaction sequence, quality control standard and procedure adopts this method of manual, micropipette processing.

FIGS. 1 and 2 illustrate the use of a single pipette tip 13, mounted at the respective insertion nozzle 14 and 15 of the pipettors 10 and 11. A technical description of state of the art tips is provided In U.S. Pat. No. 4,707,337, noting particularly prior art FIGS. 1 to 4. It will be noted in FIGS. 1 and 2 of the present application that the high volume device 10 has a short, broad nozzle 14, whereas the low volume pipettor has a longer, narrower nozzle 15. In each case, the available volume within the tip for receiving fluid corresponds to the total capacity of the pipettor (20 or 200 microliters). In the case of the P20, the insert nozzle extends deep within the pipet tip volume to a point which leaves a volume slightly larger than 20 microliters (see FIG. 4). Similarly, the P200 terminates at an upper portion of the nozzle, leaving a large volume slightly greater than 200 microliters (see FIG. 3). The limited withdrawal capacity of the pipettor prevents the fill chamber from receiving too much specimen. Therefore, the specimen is usually not contaminated by direct contact with the nozzle of the pipettor. This configuration also minimizes the void space between the nozzle of the pipettor and the top fluid level within the pipette tip. Lesser void space facilitates better accuracy in fluid transfer.

The actual volume of transferred fluid is controlled by the fine adjustment mechanism 16 and 17 within the pipettor. For example, if the lab technician wants precisely 8 microliters of specimen, he selects the P20 instrument, attaches the pipette tip 13, and makes an appropriate adjustment 17 to dial in 8 microliters. Similarly, if the aliquot is 85 microliters, the P200 is selected and adjusted accordingly 18. The same tip 13 can be inserted on either instrument because the open volume of the pipette tip is unrestricting with respect to insertion of the long versus short insert nozzle of the pipettor. A similar comment applies to the P100 (not shown).

Although direct contact of the specimen with the pipettor nozzle is usually precluded by careful technique, there is always some possibility of contamination by an aerosol effect. This results when some of the liquid vaporizes and forms droplets which are carried into contact with the nozzle by air movement. Where potential aerosol contamination is a concern, filtered pipette tips should be used. FIGS. 3 and 4 show current filtered pipet tips used with the high and low volume pipettors 21 and 22 respectively. The filter elements 23 and 24 act as a barrier against inadvertent passage of the specimen to the pipettor nozzle. U.S. Pat. No. 5,156,811 discusses the value of a filter element in pipetting operations, particularly where specimen sources are very limited, or where high risk factors exist such as with HIV testing and nucleic acid amplification reactions.

Although a single tip 13 had been suitable for nonfiltered applications, the presence of the filter within the tip body required two different insert volumes to receive the nozzle of the pipettor. For example, it is clear from FIGS. 3 and 4 that insert nozzle 15 of the low volume pipettor would be blocked from full insertion within the insert volume 26 of pipette tip 21 by the filter element 23. This rearward position for the filter 23 is required to provide the desired 200 microliters volume. This volume must remain open and free of any foreign object that might contaminate the specimen. Therefore this 20 microliters tip is not useful with the P200 pipettor 10.

Furthermore, the differing volumes of the 20 microliters and 200 microliters applied within the same tapering body necessitated the use of filter elements 23 & 24 having unequal diameters. Positioning the filter element 23 at the rearward end of the pipette tip required a much larger diameter to effectively seal the fluid chamber than did the filter 24 for the smaller 20 microliters volume in a forward portion of the tip. The necessity of two different sized filters led to a natural conclusion that two separate, prepackaged pipette tips would be required to service the respective 20 microliters and 200 microliters pipettors.

Accordingly, the commercial development of the filtered embodiments resulted in two separate tips as shown in FIGS. 3 and 4. Today, virtually all manufacturers follow this established pattern of using separate, prepackaged, filtered pipette tips for the respective high and low volume pipettors. Therefore, when a person skilled in the art is thinking low volume pipette transfer, he pictures a long pipettor shaft or nozzle 15 which seats deep within a long insert chamber of the pipette tip. This low volume measurement is consistently characterized by use of a tip that has a filter 24 deep in the tip body 22. On the other hand, when an individual wants to use a high volume pipettor, he pictures a tip 26 with a large fill chamber, which places the filter 23 high in the tip body, with little space available for the pipettor insert end.

These traditional perceptions and longstanding practices have led to a common laboratory protocol of maintaining large inventories of both high and low volume, filtered pipette tips. This practice increases procurement costs, as well as storage expense and overhead for such laboratories. Furthermore, the side-by-side presence of two different tips having incompatible filter elements may lead to mistaken use of the wrong tip, resulting in possible contamination of the specimen in the pipettor. Specifically, when a 20 microliters tip is erroneously placed on a 200 microliters pipettor, the specimen is likely to be drawn into the filter material, requiring that both the tip and the valuable specimen be discarded.

Finally, it is apparent that the use of two separate support racks or containers for the respective 20 and 200 microliters pipette tips will approximately double the time of exposure of open pipette racks to environmental contamination. For example, until the container or rack of each tip size is opened, each tip remains in a sterile container. However, once the first tip is removed, the remaining tips in the rack are exposed to the environment. Because two different filtered tips are currently required to service the micro volume range, two separate containers will be open to the environment, enhancing the likelihood of contamination. Because these respective tips are being used up at a slower rate (as compared to the unfiltered tip of the same size), adverse exposure to the environment is extended.

OBJECTS AND SUMMARY OF THE INVENTION

It is therefore an object of the present invention to provide an improved, filtered, micro-pipette tip for use within the range of either a low volume or high volume micropipettor.

It is a further object of this invention to provide a filtered, micro-pipette tip which may be interchangeably applied to either a 20 microliters, 100 microliters, or 200 microliters pipettor without contact of the pipettor nozzle with the filter element.

It is yet another object of this invention to provide such an interchangeable tip which does not require any modification to existing pipettor devices designed for use with conventional 20 microliters, 100 ul and 200 microliters pipette tips.

A still further object is to provide a tip having separate stages of containment for submicroliter and low/high volume microliter ranges.

These and other objects are realized in a micro volume, filtered pipette tip device useful with either of two respective pipettors comprising (i) a manual, air displacement pipettor operable within the approximate range of 0 to 20 microliters and having a relatively long insert nozzle, and (ii) a manual, air displacement pipettor operable within the approximate range of 20 to 200 microliters and having a relatively short insert nozzle. The pipette tip body includes a mounting end, an intermediate section, a distal fluid contacting end, and an axial bore including collinear insert and fill chambers extending in continuous, tapering configuration from said mounting end to the fluid contacting end. A filter means is positioned within the axial bore in the intermediate section at a location to provide a dividing barrier between the insert and fill chambers of the pipette tip device. The fill chamber extends from the fluid contacting end to a distal side of the filter means and has a volume of at least 150 microliters and preferably 200 microliters. The insert chamber provides a tapering, internal wall structure configured to receive a terminal insert portion of each of the two respective pipettors in a snug, sealed fit within the insert chamber. The tip device includes a filter means which is positioned sufficiently deep within the axial bore and intermediate section of the pipette tip device to allow the terminal end of the insert portion of either of the two respective pipettors to seat within the insert chamber without contacting the filter means. A pipette tip having at least three staged volumes for receiving submicroliter and microliter volumes is also disclosed.

Other objects and features of the present invention will be apparent to those skilled in the art, based on the following detailed description, in combination with the accompany drawings.

DETAILED DESCRIPTION OF THE INVENTION

Figure 1:
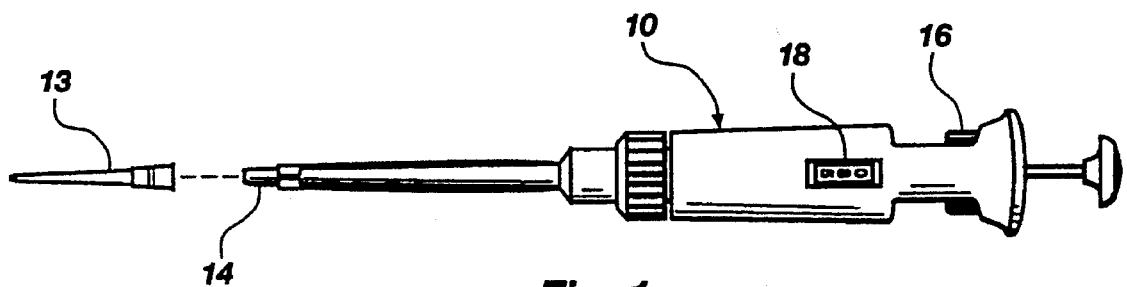
FIG. 1 graphically depicts a conventional pipettor device with a conventional non-filtered pipette tip designed for operation within the range of 0 to 20 microliters.
Figure 3:
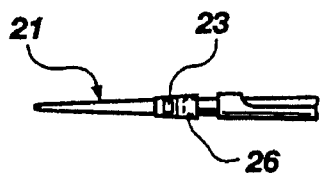
FIG. 3 represents a conventional filtered pipette tip useful for the high volume range of 0 to 200 microliters mounted on a high volume pipettor.
Figure 2:
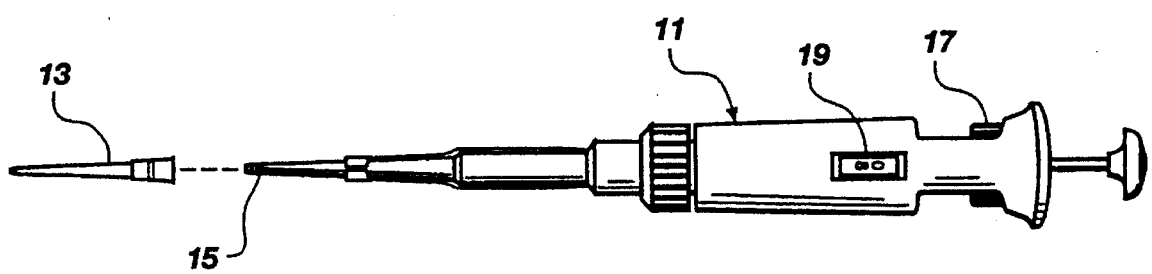
FIG. 2 graphically depicts a conventional pipettor device with a conventional non-filtered pipette tip designed for operation within the range of 0 to 200 microliters.
Figure 4:
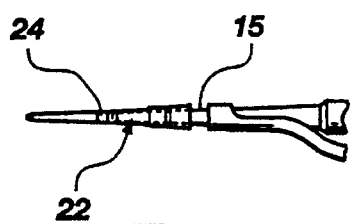
FIG. 4 represents a conventional filtered pipette tip useful for the low volume range of 0 to 20 microliters mounted on a low volume pipettor.

The present invention abandons the prior art perception that a filtered micropipette tip must have the filter positioned at different locations as illustrated in FIGS. 3 and 4. This occurs despite the fact that the inventive tip must be able to receive the long, narrow insert nozzle of the 20 microliters pipettor, as well as the shorter nozzle of the 200 microliters pipettor. It must also be recognized that redesign of the pipettor tip has not been viewed as a realistic commercial option because the purchasers of this product are persons who already own existing pipettors which dictate the shape and size of the pipette tip. Therefore, the options for variation of the tip configuration appear limited. The new pipette tip must be useful on the same pipettors that can use the variable sized 20 microliters and 200 microliters tips of the prior art. The unexpected solution of adopting a single filtered pipette tip for common use on the respective 20 and 200 microliters pipettors was even more unforeseeable in view of the fact that a single supplier of pipettors dominates the industry with the P20 and P200 models. This tends to lead those skilled in the art to conform to supplier specifications and to follow trends in the industry that are specific to these devices. This is evidenced by the fact that all of the following worldwide suppliers of micro-volume pipette tips conform to the two-tip approach for filtered pipette tips:

Sorenson BioScience (formerly Multi-Technology, Inc.)
Rainin Instruments
Elkay Lab Products
Labcon Inc.

USA Scientific
Molecular Bio Products
National Scientific
Griener Plastics
Ulster Scientific
Corning/Costar
Energreen
Stockwell Scientific There appear to be no significant exceptions to this practice. Indeed, the present inventors have followed this same trend for many years, supplying two different tips for the respective 20 microliters 100 ul and 200 microliters manual, air displacement pipettor devices. Total sales quantities of these respective tips by applicant alone (identified under the trademark MULTI-Tip) have been in the billions.

Nevertheless, the present inventors have developed a micro volume, filtered pipette tip device useful with either of the two respective pipettors comprising (i) a manual, air displacement pipettor operable within the approximate range of 0 to 20 microliters and having a relatively long insert tip, and (ii) an intermediate 1 to 100 ul pipettor and (iii) a manual, air displacement pipettor operable within the approximate range of 20 to 200 microliters and having a relatively short insert tip. This tip meets the structural demands of prior art devices, as well as providing the convenience and economy of a single tip system.

The inventive tip comprises a pipette tip body 30 having a mounting end 31, an intermediate section 32, a distal fluid contacting end 33, and an axial bore 34. The axial bore includes a collinear insert chamber 34a and a fill chamber 34b extending in continuous, tapering configuration from said mounting end 31 to the fluid contacting end 33. The tapering configuration is compatible with the angular taper of both the P20 and P200 versions of current pipettors. Nevertheless, only one filter 35 is required because of the elongation of the intermediate section of the tip.

This filter 35 is positioned within the axial bore in the intermediate section against a locking ring 36 to secure the filter in place. The use of the positioning rib enables rapid and accurate placement of the filter at a predetermined location that will ensure proper relative positioning of each of the insertion tips of the pipettors 10 & 11, as well as maintenance of proper volumes in the fill chamber. This position of the filter corresponds to a dividing barrier fixed between the insert and fill chambers of the pipette tip device to prevent aerosol contamination. Numerous filter materials may be selected; however, the filter means of the present embodiment comprises a filter membrane formed of polypropylene or self sealing (nonmechanical shut off) material.

In all instances, the filter means 35 is positioned sufficiently deep within the axial bore 34 and intermediate section 32 of the pipette tip device to allow the terminal end 40 and 41 of the insert portion of either of the two respective pipettors to seat within the insert chamber 44 without contacting the filter means.

On an opposite side from the insert chamber 44 is the fill chamber 45. The fill chamber 45 extends from the fluid contacting end 46 of the tip to a distal side of the filter means 35. This chamber provides a volume of at least 150 microliters, and preferably 200 microliters. Because of the ample fill chamber, either pipettor device can be used without concern of overfill. Indeed, a major advantage of this invention is the elimination of common losses which occur as a technician accidentally inserts a 20 microliters tip on a 200 microliters pipettor. Whereas the 200 microliters pipettor with 20 microliters tip would draw precious specimen recklessly into the filter, the present invention insures that full fill volume of the pipettor is available within the tip. In the latter case, the excess specimen drawn into the tip may simple be voided to its storage container for future use without contamination from either the pipettor nozzle or the filter.

The insert chamber includes a tapering internal wall structure 48 configured to receive a terminal insert portion 40 and 41 of each of the two respective pipettors in a snug, sealed fit within the insert chamber. Therefore, the same insertion techniques which have been regularly applied by lab technicians of the past years may continue without significant deviation. This feature of the present invention is important for commercial acceptability. Traditional practice has resulted in numerous technical routines which have been adopted in countless instruction manuals, research protocols and al habits of practice for each technician.

Figure 7:
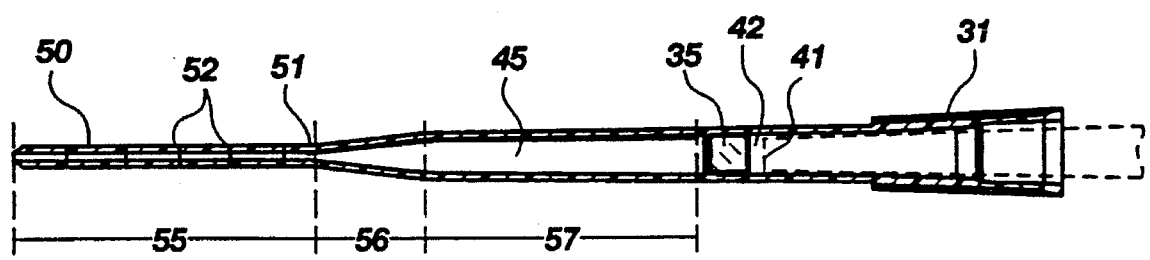
FIG. 7 depicts a staged-volume, filtered tip mounted on a conventional 20 microliters pipettor.

As illustrated in FIG. 7, the pipette tip body may further include a capillary tip 50 extending from the distal fluid contacting end 51 to provide an extension of the fill chamber for holding less than 10 microliters. This not only allows better delivery or extraction of minimal quantities of a specimen, but also permits more accurate visual estimation of the aliquot portion. Fabrication of this capillary tip as part of the tip body is fully disclosed in the previously referenced U.S. Pat. No. 4,707,337, as well as in other publications available to the public. For additional accuracy, the capillary tip may include graduation means 52 for estimating actual volume contained within the capillary tip. Similar graduation marks may be used on the rest of the fill chamber.

A significant feature of the present invention is configuration of the tip body with segmented stages that facilitate pipetting of liquids in any one of the submicro, micro or macro quantities. For example, FIG. 7 discloses a tip body which is divided into three stages 55, 56 and 57. The capillary tip 50 enables extraction of nanoliter volumes in a controlled and accurate manner, based on use of a prescribed pipettor device for this quantity. This same tip could be used, however, for microliter measurements which could extend into the first tapering stage 56 of the tip. This first tapering stage 56 could serve as the low range fill chamber for micro-pipetting as discussed above from 5 to 20 microliters. Hereagain, graduation marks may assist in estimation of transferred fluid. Finally, the second tapering stage 57 corresponds to the high volume fill chamber of up to 200 microliters. Accordingly, this embodiment, provides three discreet quantity levels which are facilitated by this single pipette tip. It will be apparent that additional stages could be structured to meet particular needs of any pipetting procedure.

Although the present invention may be embodied in numerous dimensions, a preferred embodiment is represented by the following configuration. The pipette tip has a length of approximately 2.5 inches and a inner diameter at the mounting end of approximately 0.212 inches. The capillary section 55 has a length of 0.693 inches with a 2 microliters capacity. The first stage taper 56 has a length of 0.419 inches and an angular taper of approximately 6.5 degrees. The volume of this stage is approximately 30 microliters. The second stage taper 57 is at approximately 0.5 degrees, with a length of 0.861 inches. The fill chamber to this point represents approximately 202 microliters.

Figure 5:
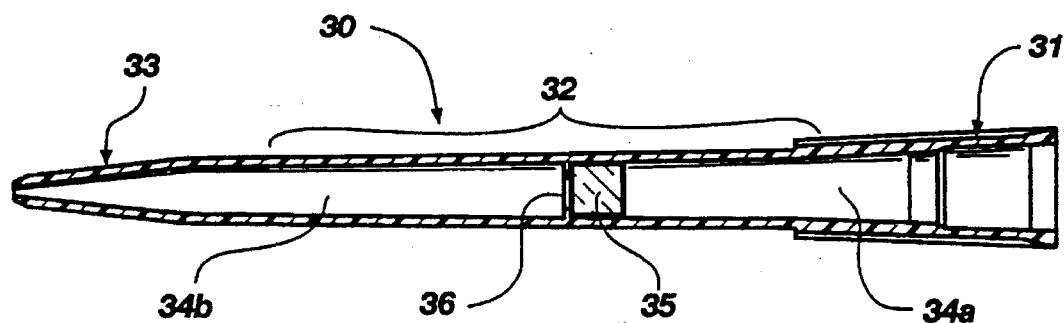
FIG. 5 illustrates a cross-section of a preferred embodiment of a filtered, micro-pipette tip in accordance with the present invention.
Figure 6:
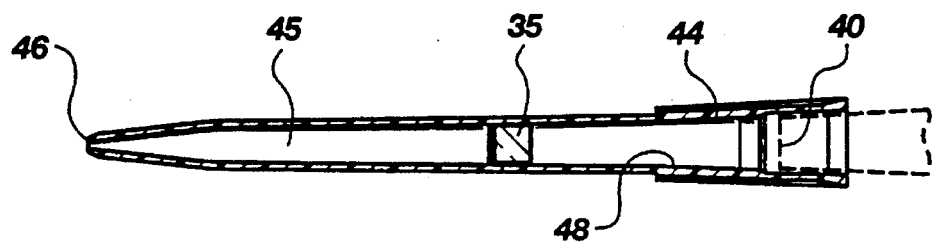
FIG. 6 depicts the filtered tip of FIG. 5 mounted on a conventional 200 microliters pipettor.

It will be apparent to those skilled in the art, that the configuration along the length of the pipette tip device may have variable taper rates. For example, the illustrated embodiments in FIGS. 5, 6, and 7 have a greater rate of taper at the respective mounting and contacting ends as compared with a lesser rate of taper within the intermediate section. This facilitates the positioning of the filter means at a stable position against a locking ring.

It will also be apparent to those skilled in the art that other means for positioning the filter may be developed. The preferred embodiment is generally characterized by an axial bore which includes an internal wall within the intermediate section having an inwardly projecting ring at an approximate midpoint of the intermediate section. This functions to restrain insertion of the filter means beyond the retaining or locking ring. It also assists in sealing the periphery of the filter.

The various structures identified above form part of an inventive methodology of using a single pipette tip device with either of the two respective pipettors comprising (i) a manual or electronic, air displacement pipettor operable within the approximate range of 0 to 20 microliters, and (ii) a manual or electronic, air displacement pipettor operable within the approximate range of 20 to 200 microliters. This method comprises the steps of (i) selecting a pipette tip body having a mounting end, an intermediate section, a distal fluid contacting end, and an axial bore including opposing insert and fill chambers extending in tapering configuration from the mounting end to the fluid contacting end; (ii) inserting a filter means within the axial bore in the intermediate section to provide a dividing barrier between the opposing insert and fill chambers of the pipette tip device wherein a resulting volume of the fill chamber is at least 150 microliters; and (iii) alternatively inserting a terminal insert portion of each of the two respective pipettors in a snug, sealed fit within the insert chamber without contacting the filter means.

It is to be understood that the recitation of preferred embodiments as set forth above are not to be considered as limiting, but are merely exemplary of the inventive principles applied as defined in the following claims.

I claim:

1. A method of using a single pipette tip body with each of three respective pipettors selected from the group consisting of (i) an air displacement pipettor operable within the approximate range of 0 to 20 microliters, (ii) an air displacement pipettor operable within the approximate range of 20 to 200 microliters, and (iii) an intermediate pipettor operable within the range of 0–100 microliters, said method comprising the steps of:

selecting a pipette tip body having a mounting end, an intermediate section, a distal fluid contacting end, and an axial bore including opposing insert and fill chambers extending in tapering configuration from said mounting end to the fluid contacting end;

inserting a filter means within the axial bore in the intermediate section to provide a dividing barrier between the opposing insert and fill chambers of the pipette tip device wherein a resulting volume of the fill chamber is at least 200 microliters; and alternatively inserting a terminal insert portion of each of the three respective pipettors in a snug, sealed fit within the insert chamber of the selected pipette tip body without contacting the filter means.

2. A method as defined in claim 1, further comprising the step of inserting the filter means within the axial bore until an inwardly projecting, centrally positioned blocking ring within the intermediate section inhibits further foreword movement of the filter means along the axial bore.

3. A pipette device for pipetting micro volumes of liquid, said device comprising:

a pipettor selected from a group of manual, air displacement pipettors having a tapering insert tip for insertion into a pipette tip having a tapering insert chamber, said pipettor group consisting of (i) a pipettor operable to pipette volumes up to and including 20 microliters and having a relatively long insert tip, (ii) a pipettor operable to pipette volumes up to and including 200 microliters and having a relatively short insert tip, and (iii) an intermediate pipettor operable to pipette volumes up to and including 100 microliters;

a single pipette tip body having a mounting end, an intermediate section, a distal fluid contacting end, and an axial bore including collinear insert and fill chambers extending in continuous tapering configuration from said mounting end to the fluid contacting end; and a filter means positioned within the axial bore in the intermediate section, the position of said filter means providing a dividing barrier between the insert and fill chambers of the pipette tip device;

said fill chamber extending from the fluid contacting end to a distal side of the filter means and having a volume of at least 200 microliters;

said insert chamber having a tapering internal wall structure configured to receive a terminal insert portion of each of the three respective pipettors of 20 microliters, 200 microliters and 100 microliters in a snug, sealed fit within the insert chamber;

said single pipette tip being removably inserted on at least one of the respective pipettors with the filter means being positioned sufficiently deep within the axial bore and intermediate section of the pipette tip body to allow the terminal end of the insert portion of each of the three respective pipettors to seat within the insert chamber without contacting the filter means.

4. A device as defined in claim 3, wherein the pipette tip body further includes a capillary tip extending from the distal fluid contacting end to provide an extension of the fill chamber for holding less than 10 microliters.

5. A device as defined in claim 4, wherein the capillary tip includes graduation means for estimating actual volume contained within the capillary tip.

6. A device as defined in claim 3, further comprising a pipette tip body having at least three segmented stages representing three respective quantitative ranges of specimen volume, each segmented stage being represented by a different-geometric configuration of the tip body.

7. A device as defined in claim 6, wherein the respective segmented stages include a capillary section coupled to a sharply tapering mid-section of larger volume, said mid-section being coupled to a larger volume primary tip body of more gradual taper than the mid-section.

8. A device as defined in claim 7, wherein the-capillary section is configured to withdraw sub-microliter volumes, the mid-section is configured to receive microliter volumes, and the primary tip body is configured to receive microliter volumes and greater.

9. A device as defined in claim 8, wherein the rate of taper for the mounting end is approximately 3 degrees per side.

10. A device as defined in claim 8, wherein the rate of taper for the contacting end is approximately 3 degrees per side.

11. A device as defined in claim 8, wherein the rate of paper for the intermediate Section is approximately 6.5 degrees per side.

12. A device as defined in claim 7, wherein the configuration along the length of the pipette tip device comprises a greater rate of taper at the respective mounting and contacting ends as compared with a lesser rate of taper within the intermediate section.

13. A device as defined in claim 3, wherein the pipette tip has a length of approximately 6.5 cm and a inner diameter at the mounting end of approximately 5 mm.

14. A device as defined in claim 3, wherein the axial bore includes an internal wall within the intermediate section which includes an inwardly projecting locking ring operable as a stopping member to restrain insertion of the filter means beyond the projecting ring.

15. A device as defined in claim 14, wherein the inwardly projecting ring is positioned at an approximate midpoint along the pipette tip device.

16. A device as defined in claim 3, wherein the filter means comprises a composition of polypropylene and/or starch copolymer.

* * * * *